United States Patent [19]

Kita

[11] 4,339,586
[45] Jul. 13, 1982

[54] PRODUCTION OF PYRIDOXINE

[75] Inventor: Harumi Kita, Hikari, Japan

[73] Assignee: Takeda Chemical Industries, Ltd., Osaka, Japan

[21] Appl. No.: 223,923

[22] Filed: Jan. 9, 1981

[30] Foreign Application Priority Data

Jan. 11, 1980 [JP] Japan .................................. 55/2372

[51] Int. Cl.³ .......................................... C07D 213/67
[52] U.S. Cl. .................................................... 546/301
[58] Field of Search ........................................ 546/301

[56] References Cited

U.S. PATENT DOCUMENTS 3,669,984  6/1972  Schaeren ........................ 260/307 R

FOREIGN PATENT DOCUMENTS 1293843 10/1972 United Kingdom ................ 546/301

*Primary Examiner*—Alan L. Rotman
*Attorney, Agent, or Firm*—Wenderoth, Lind & Ponack

[57] ABSTRACT

Pyridoxine or its acid addition salt is produced by reacting 4-carboxymethyl-5-substituted oxy-oxazoles with 4,7-dihydro-1,3-dioxepines in the presence of a compound of the formula

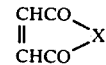

wherein X is oxygen, —NH—, or —NH—NH— and, then, subjecting the resultant compound to hydrolysis. This process offers industrially more advantageous production of pyridoxine than hitherto known processes.

4 Claims, No Drawings

PRODUCTION OF PYRIDOXINE

The present invention relates to an industrially advantageous process for producing pyridoxine, a pyridine derivative.

At the present time, the industrial production of pyridoxine is being practiced by the reaction of a 4-methyl-5-lower alkoxyoxazole with an ethylene compound, or the reaction of a 4-carboxymethyl-5-lower alkoxymethyloxazole with a dienophilic compound (U.S. Pat. Nos. 3,413,297 and 3,565,909). However, these processes are not necessarily considered industrially profitable in that the 4-methyl-5-lower alkoxyoxazole used in the former reaction as the starting compound is costly, and in that both of the reactions, in which 4,7-dihydro-1,3-dioxepines are used as a dienophilic compound, cannot produce the objective compound in high yields. A modified method involving, for example, the use of maleic acid esters as a dienophilic compound, and reduction to pyridoxine (e.g., Chemical Pharmaceutical Bulletin, Vol. 20, No. 4, pp.804 to 814, 1972), as commercially adopted, requires an expensive catalyst such as aluminum lithium hydride and sodium borohydride.

The present inventor, after extensive investigation of a process enabling these reactions to be carried out with high yields and in an economically advantageous way, found that by allowing maleic anhydride, maleimide or maleic hydrazide to coexist in the reaction of 4-carboxymethyl-5-substituted-oxyoxazoles with 4,7-dihydro-1,3-dioxepines, the yield can be remarkably improved, with satisfactory results, and has thus completed the present invention.

Thus, the present invention relates to an improved process for producing pyridoxine, or its acid addition salt, which comprises reacting a compound of the formula (I):

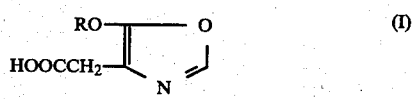

(wherein R is a hydrocarbon group) with a compound of the formula (II):

(wherein $R_1$ and $R_2$ independently of each other stand for hydrogen or a lower alkyl group) in the presence of a compound of the formula (III):

(wherein X is oxygen, —NH— or —NH—NH— group) and, then, subjecting the resultant compound to hydrolysis.

In the formula (I) as described above, examples of the hydrocarbon group include hydrocarbon groups containing up to 10 carbon atoms, for example, straight-chain or branched alkyl groups such as methyl, ethyl, propyl and isopropyl; cycloalkyl groups such as cyclohexyl; alkenyl or alkynyl groups such as vinyl, propenyl, isopropenyl, butenyl, pentenyl, ethynyl and propynyl; aryl groups such as phenyl and naphthyl; and aralkyl groups such as benzyl; but any type of hydrocarbon groups may be employed, unless they adversely affect the reaction. Among these hydrocarbons, the ones which, particularly, are often employed and produce satisfactory results are typified by lower alkyl groups having 1 to 3 carbon atoms, such as methyl and ethyl.

In the general formula (II), the lower alkyls represented by $R_1$ and $R_2$ include lower alkyl groups having 1 to 5 carbon atoms, preferably 1 to 3 carbon atoms such as methyl, ethyl, propyl and isopropyl. The symbols $R_1$ and $R_2$, together with the adjacent carbon atom, may jointly be 5- or 6-membered cycloalkyl ring. Of the compounds represented by the general formula (II), particularly desirable are 4,7-dihydro-1,3-dioxepine or a compound of the formula (II) wherein $R_1$ and $R_2$ both are hydrogen; 2-isopropyl-4,7-dihydro-1,3-dioxepine or a compound of the formula (II) wherein one of $R_1$ and $R_2$ is hydrogen and the other is isopropyl; and 2,2-dimethyl-4,7-dihydro-1,3-dioxepine or a compound of the formula (II) wherein $R_1$ and $R_2$ both are methyl.

The present invention is conducted by subjecting the above-mentioned compounds of the general formulas (I) and (II) to the so-called Diels-Alder reaction in the presence of the compund (III). As the compound of the general formula (III), any of maleic anhydride, maleimide and maleic hydrazide may be employable. The method of the present invention can be allowed to proceed by employing the normal reaction conditions applicable to the Diels-Alder reaction. Such conditions may be exemplified by the methods which involve mixing the compounds of the general formulas (I), (II) and (III), followed by either heating directly without a solvent or heating in an inert solvent such as ketones, e.g. acetone and methyl ethyl ketone, acetonitrile, dimethylformamide, and ethers, e.g. dimethyl ether and diethyl ether. The reaction normally proceeds at about 50° to 250° C. and most desirably at about 100° to 210° C. In the case of 2-isopropyl-4,7-dihydro-1,3-dioxepine being used as a compound of the general formula (II), the reaction is allowed to proceed preferably at the refluxing temperature of the reaction mixture. The reaction time varies with the reaction temperature and furthermore with the type of starting compounds and, normally, the reaction goes to conclusion within 1 to 10 hours. The reaction proceeds either in the atmosphere or under pressure. Side reactions, e.g., polymerization, can be suppressed by replacing the air in the reaction vessel with an inert gas such as nitrogen and argon.

It is sufficient to allow a compound of the general formula (III) to coexist in a catalytic quantity, and the reaction proceeds smoothly, particularly when the compound is allowed to coexist in a proportion of about 1/100 to ⅓ mole, preferably 1/50 to 1/10 mole against 1 mole of the oxazole of the general formula (I). The dioxepine of the general formula (II) is preferably added at a ratio of about 2 to 20 times, particularly about 15 times, the molar quantity of the oxazole of the general formula (I). In this case, the excessive dioxepine (II) can be recovered by distillation after the conclusion of the reaction, and the distillate can be repeatedly subjected to the reaction with the compound (I).

The compound of the general formula (IV):

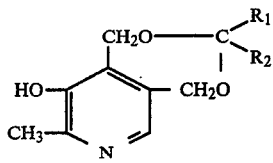

(wherein the symbols in the formula are as defined hereinbefore) as obtained through the above-mentioned reaction is hydrolyzed by a conventional procedure to lead to pyridoxine. For example, the excessive dioxepine is distilled off after the conclusion of the reaction, and the resultant residue is treated with an acid catalyst, directly or after being purified if necessary, thereby yielding pyridoxine. As examples of the acid catalyst there may be mentioned inorganic acids such as hydrochloric acid, sulfuric acid and phosphoric acid, and organic acids such as acetic acid, formic acid and organic sulfonic acid, and, in particular, dilute hydrochloric acid is often used. In the case of the treatment with dilute hydrochloric acid, relatively mild conditions of, for example, 50° to 70° C. for a period within several hours, are satisfactory. By distilling off the water from the hydrolysis treatment solution under reduced pressure and recrystallizing the resultant residue from a suitable solvent, there is obtained an acid addition salt of pyridoxine in a high yield.

The present invention offers the advantages, such as permitting the utilization of oxazolacetic acid derivatives via aspartic acid derivatives, realizing high yields in the Diels-Alder addition reaction and yielding pyridoxine from the resultant adduct through a simple hydrolysis treatment, and may be said to be an excellent industrial production process.

The examples are given below to illustrate the present invention more specifically, but are not to be construed to limit the scope of the present invention.

EXAMPLE 1

In a 200-ml four-necked flask equipped with a thermometer and a cooling tube were mixed 106.7 g (0.75 mole) of 2-isopropyl-4,7-dihydro-1,3-dioxepine, 8.56 g (0.05 mole) of 5-ethoxy-4-oxazolylacetic acid and 0.50 g (0.005 mole) of maleic anhydride, and the mixture was refluxed under nitrogen streams for 3 hours on an oil bath externally maintained at a temperature of 190° C. After the conclusion of the reaction, the mixture was distilled under reduced pressure to recover unreacted materials, and the residue was dissolved in 15 ml of methyl alcohol. Then, 10 ml of 3N-hydrochloric acid was added to the solution, and the mixture was allowed to stand overnight at room temperature, followed by distilling off the alcohol under reduced pressure. To the resultant residue was added 15 ml of 3N-hydrochloric acid and, after heating at 70° C. for 20 minutes, the water was distilled off under reduced pressure. Ethyl alcohol was added to the residual solution, and the solution was allowed to stand overnight at 5° C. The crystals were separated and dried. The melting point of thus obtained crystals was found to be 201° to 204° C., and the infrared and NMR spectra thereof were in accordance with those of pure pyridoxine hydrochloride. Yield 8.25 g (80.3%).

EXAMPLE 2

In a 200-ml, stainless steel autoclave were mixed 106.7 g of 2-isopropyl-4,7-dihydro-1,3-dioxepine, 8.56 g of 5-ethoxy-4-oxazolylacetic acid and 0.50 g of maleic anhydride, and, after replacing the air in the autoclave with nitrogen gas to a satisfactory extent, the mixture was heated at the external temperature of 190° C. for 3 hours. By effecting hereinafter the same procedures as described in Example 1, there was obtained 8.48 g (82.5% of yield) of pyridoxine hydrochloride.

EXAMPLE 3

In a 200-ml four-necked flask equipped with a thermometer and a cooling tube were mixed 106.7 g of 2-isopropyl-4,7-dihydro-1,3-dioxepine, 8.56 g of 5-ethoxy-4-oxazolylacetic acid and 0.10 g (0.001 mole) of maleic anhydride, and the mixture was refluxed under nitrogen streams for 3 hours on an oil bath externally maintained at a temperature of 190° C. in order to carry out the reaction. After the conclusion of the reaction, the mixture was distilled under reduced pressure to recover unreacted materials, and the residue was dissolved in 15 ml of methyl alcohol. Then, 10 ml of 3N-hydrochloric acid was added to the solution, and the mixture was allowed to stand overnight at room temperature, followed by distilling off the alcohol under reduced pressure. To the resultant residue was added 15 ml of 3N-hydrochloric acid and, after heating at 70° C. for 20 minutes, the water was distilled off under reduced pressure. Ethyl alcohol was added to the residual solution, and the solution was allowed to stand overnight at 5° C. The crystals were separated and dried. The crystals obtained in this manner exhibited a melting point of 201° to 204° C., and the infrared and NMR spectra were in accordance with those of pure pyridoxine hydrochloride. Yield 8.53 g (83.0%).

EXAMPLE 4

In a 200-ml, stainless steel autoclave were mixed 106.7 g of 2-isopropyl-4,7-dihydro-1,3-dioxepine, 8.56 g of 5-ethoxy-4-oxazolylacetic acid and 0.25 g of maleic anhydride, and, after replacing the air in the autoclave sufficiently with nitrogen gas, the mixture was heated at the external temperature of 190° C. for 3 hours. By effecting hereinafter the same procedures as described in Example 1, there was obtained 8.64 g (84.0%) of pyridoxine hydrochloride.

EXAMPLE 5

In a 200-ml, stainless steel autoclave were mixed 106.7 g of 2-isopropyl-4,7-dihydro-1,3-dioxepine, 8.56 g of 5-ethoxy-4-oxazolylacetic acid and 0.56 g of maleic hydrazide, and, after replacing the air in the autoclave with nitrogen gas to a satisfactory extent, the mixture was heated at the external temperature of 190° C. for 3 hours. By effecting hereinafter the same procedures as described in Example 1, there was obtained 7.71 g (75.0%) of pyridoxine hydrochloride.

EXAMPLE 6

In a 200-ml, four-necked flask equipped with a thermometer and a cooling tube were mixed 75.2 g of 4,7-dihydro-1,3-dioxepine, 8.56 g of 5-ethoxy-4-oxazolylacetic acid and 0.49 g of maleimide, and the mixture was refluxed in nitrogen streams for 3 hours over an oil bath externally maintained at 190° C. so as to conduct the reaction. By effecting hereinafter the same procedures as described in Example 1 there was obtained 80.7 g (78.5%) of pyridoxine hydrochloride.

REFERENCE EXAMPLE

In the same manner, 106.7 g of 2-isopropyl-4,7-dihydro-1,3-dioxepine and 8.56 g of 5-ethoxy-4-oxazolylacetic acid were reacted with no catalyst, thereby affording 2.05 g of pyridoxine hydrochloride (20.0%).

What is claimed is:

1. A process for producing pyridoxine or its pharmaceutically acceptable acid addition salt, which comprises reacting a compound of the formula

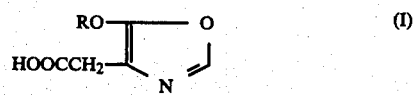 (I)

wherein R is alkyl of 1 to 3 carbon atoms, with a compound of the formula

 (II)

wherein $R_1$ and $R_2$, independently of each other, are hydrogen or alkyl of 1 to 5 carbon atoms, or $R_1$ and $R_2$, together with the adjacent carbon atom, may form a 5- or 6-membered cycloalkyl ring, at about 50° to 250° C., in the presence of about 1/100 to ½ mole, per mole of said (I), of a compound of the formula

 (III)

wherein X is oxygen, —NH— or —NH—NH—, and subjecting the resultant compound to hydrolysis in the presence of an acid catalyst.

2. A process as claimed in claim 1, wherein the alkyl group designated by the symbols $R_1$ and $R_2$ is, independently of each other, methyl, ethyl, propyl or isopropyl.

3. A process as claimed in claim 1, wherein one of $R_1$ and $R_2$ is hydrogen and the other is isopropyl.

4. A process as claimed in claim 1, wherein the compound of the formula

is maleic anhydride.

* * * * *